(12) United States Patent
Florio

(10) Patent No.: US 7,117,036 B2
(45) Date of Patent: Oct. 3, 2006

(54) USING ACTIVITY-BASED REST DISTURBANCE AS A METRIC OF SLEEP APNEA

(75) Inventor: Joseph J. Florio, La Canada, CA (US)

(73) Assignee: Pacesetter, Inc., Sylmar, CA (US)

(*) Notice: Subject to any disclaimer, the term of this patent is extended or adjusted under 35 U.S.C. 154(b) by 658 days.

(21) Appl. No.: 10/185,776

(22) Filed: Jun. 27, 2002

(65) Prior Publication Data

US 2004/0002742 A1   Jan. 1, 2004

(51) Int. Cl.
*A61N 1/365* (2006.01)
*A61N 1/37* (2006.01)
*A61B 5/11* (2006.01)

(52) U.S. Cl. ............................................ 607/19; 607/18
(58) Field of Classification Search ........ 600/508–528; 607/1–28
See application file for complete search history.

(56) References Cited

U.S. PATENT DOCUMENTS

| 5,476,483 | A | | 12/1995 | Bornzin et al. |
| 5,485,851 | A | * | 1/1996 | Erickson ............ 600/529 |
| 5,522,862 | A | | 6/1996 | Testerman et al. |
| 5,593,431 | A | * | 1/1997 | Sheldon ............ 607/19 |
| 6,641,542 | B1 | * | 11/2003 | Cho et al. ......... 600/529 |
| 6,881,192 | B1 | * | 4/2005 | Park ................ 600/529 |

FOREIGN PATENT DOCUMENTS

EP   0702978 A3   3/1996

* cited by examiner

Primary Examiner—Robert E. Prezzuto
Assistant Examiner—Kristen Mullen

(57) ABSTRACT

An implantable cardiac device is programmed to monitor short term activity changes that occur while a patient is at rest to produce a sleep disturbance metric that is useful in analyzing and/or treating sleep apnea. After the implantable cardiac device confirms that a patient is at rest, the device monitors an instantaneous signal from an activity sensor to detect variances from normal rest mode activity. When the variances exceed a preset threshold for a short time period (e.g., less than 30–40 sec.), the patient is presumed to be experiencing a form of sleep disturbance as opposed to conscious or wakeful activity. These short term events are recorded as sleep disturbance events. The sleep disturbance metric are reported to a physician as a diagnostic to help ascertain the severity of sleep apnea or to evaluate the effectiveness of pacing therapies being applied to treat sleep apnea.

31 Claims, 5 Drawing Sheets

USING ACTIVITY-BASED REST DISTURBANCE AS A METRIC OF SLEEP APNEA

TECHNICAL FIELD

The present invention generally relates to implantable cardiac devices, and particularly, to techniques for monitoring sleep disturbances as a metric for determining severity of sleep apnea and/or for evaluating pacing therapies for treating sleep apnea.

BACKGROUND

Sleep apnea is a condition in which a person stops breathing for a short time while sleeping. Sleep apnea has multiple classifications based on the source of dysfunction. Obstructive sleep apnea results from mechanical blockage of the airway, for example, due to the weight of fatty neck tissue compressing the trachea. Central sleep apnea results from neurological dysfunction. Mixed sleep apnea has a combination of mechanical and neurological cause.

Symptoms of sleep apnea include snoring, breath holding during sleep, rapid awakening with gasping for air, morning headaches, depression, irritability, loss of memory, lack of energy, high risk of automobile and workplace accidents, and lack of high quality sleep and resulting daytime grogginess and sleepiness. Sleep apnea is rarely fatal but is linked to high blood pressure and increased probability of heart disease, stroke, and arrhythmias. Patients with coronary artery disease who have a blood oxygen level lowered by sleep-disordered breathing may be at risk of ventricular arrhythmia and nocturnal sudden death. Furthermore, sleep-disordered breathing may cause coronary artery disease and hypertension.

Various treatments exist for sleep apnea including medical device treatments, surgery, and drugs. The type of treatment depends on the type of sleep apnea. For patients who also experience heart failure or other cardiac conditions, another form of treatment that has been proposed for treating sleep apnea is pacing therapy administered by an implantable cardiac device, such as an implantable pacemaker. For this latter form of treatment, however, there remains a need to further improve the operation of implantable cardiac devices to better analyze sleep apnea and determine which types of response therapies offer more effective results.

SUMMARY

An implantable cardiac device is programmed to monitor frequency and duration of short term activity changes that occur while a patient is at rest to produce a sleep disturbance metric that is useful in analyzing and/or treating sleep apnea. In one implementation, the implantable cardiac device initially confirms that a patient is at rest using an activity sensor. The device then monitors an instantaneous signal from the activity sensor to detect variances from normal rest mode activity. When the variances exceed a preset threshold for a short time period (e.g., less than 30 sec.), the patient is presumed to be experiencing a form of sleep disturbance as opposed to conscious or wakeful activity. These short term events are recorded as sleep disturbance events. The device develops a metric for these disturbances, such as the number of sleep disturbances experienced in a specified timeframe or the frequency of their occurrence.

The sleep disturbance metrics can then be reported to a physician as a diagnostic to help ascertain the severity of sleep apnea. Additionally, under the supervision of the physician, the implantable device may be programmed to administer different types of pacing therapies in response to sleep disturbances, where the sleep disturbance metric is used to evaluate whether certain therapies are more effective at treating apnea than others.

DETAILED DESCRIPTION

Overview

In the following discussion, an implantable cardiac device is described that utilizes sleep disturbance as a metric for sleep apnea. The device is programmed to derive the sleep disturbance metric from monitoring frequency and duration of short term activity changes that occur while a patient is at rest. The device can then be programmed to administer different pacing therapies and evaluate which pacing therapies are effective at reducing sleep disturbance, thereby indirectly treating sleep apnea. In this manner, the sleep disturbance metric can be used to prescribe effective pacing treatments for sleep apnea.

Implantable cardiac devices are commonly characterized as a miniature computing device that is implanted into the body of a patient to monitor, regulate, and/or correct heart activity. Such devices include implantable cardiac stimulation devices (e.g., implantable cardiac pacemakers, implantable defibrillators) that apply stimulation therapy to the heart as well as implantable cardiac monitors that monitor and record heart activity for diagnostic purposes. The following discussion describes first an exemplary cardiac device and then a mode of operation in which sleep apnea episodes are detected, their durations are measured, and various pacing therapies are evaluated.

Exemplary Implantable Cardiac Device

Figure 1:
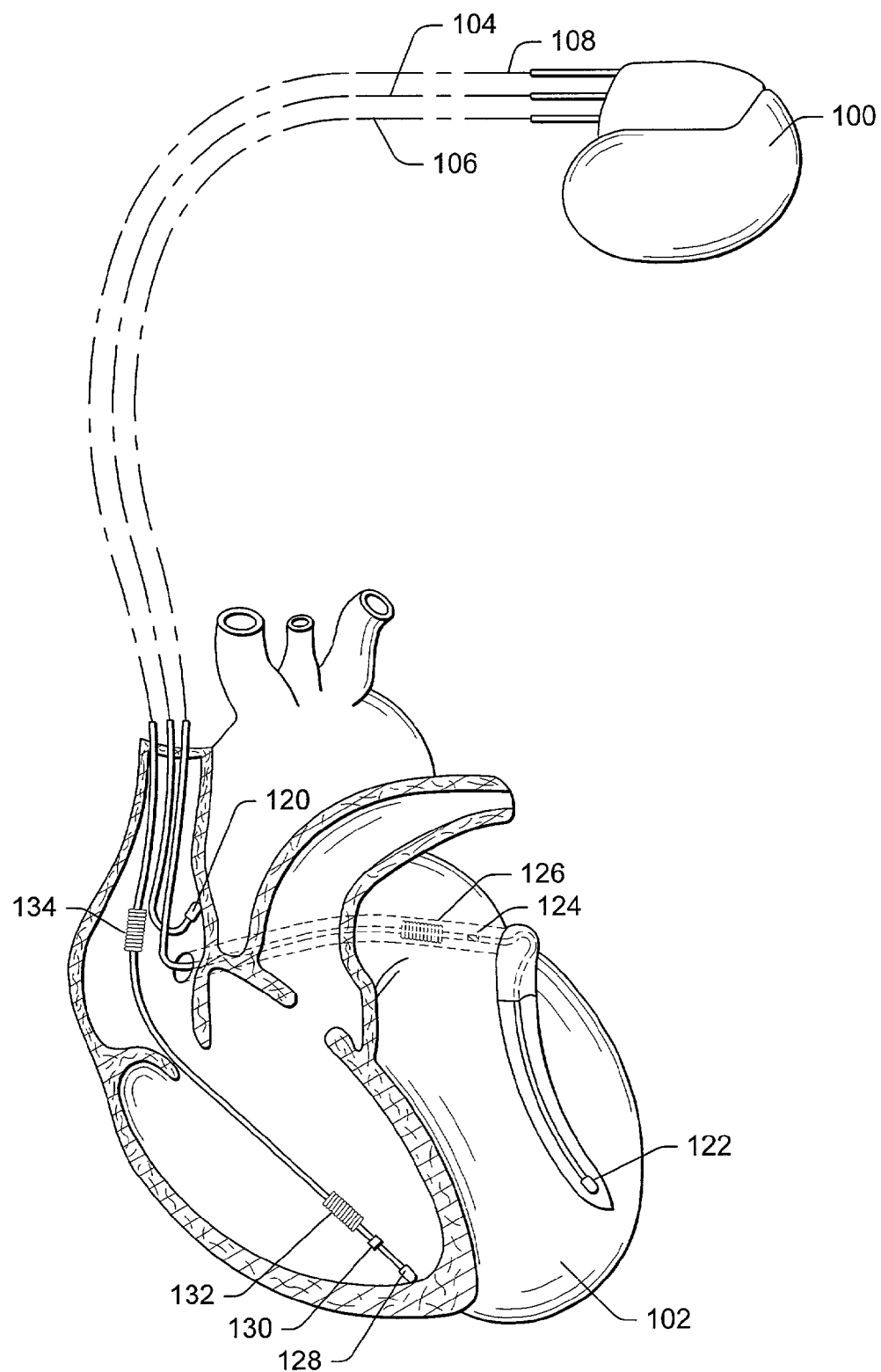
FIG. 1 is a diagrammatic illustration of an implantable cardiac device in electrical communication with a patient's heart for multi-chamber sensing and delivery of multi-chamber stimulation and shock therapy.

FIG. 1 shows an exemplary implantable cardiac device 100 in electrical communication with a patient's heart 102 for monitoring heart activity and/or delivering stimulation therapy, such as pacing therapies. Three leads—a right atrial lead 104, a coronary sinus lead 106, and a right ventricular lead 108—interconnect the device 100 with the patient's heart 102 to support multi-chamber detection and stimulation therapy.

The right atrial lead 104 supports an atrial tip electrode 120, which typically is implanted in the patient's right atrial appendage. The right atrial lead 104 enables the device to sense atrial cardiac signals and apply pacing therapy to the right atrial chamber.

The coronary sinus lead 106 positions a left ventricular tip electrode 122 adjacent to the left ventricle and/or additional electrode(s) adjacent to the left atrium, such as a left atrial ring electrode 124 and a left atrial coil electrode 126. The coronary sinus lead 106 enables the device 100 to sense left atrial and ventricular cardiac signals and administer left chamber pacing therapy. In the illustrated arrangement, the left ventricular tip electrode 122 is used to sense atrial and ventricular cardiac signals and deliver left ventricular pacing therapy. The left atrial ring electrode 124 is employed for applying left atrial pacing therapy, and the left atrial coil electrode 126 is used for shocking therapy.

The right ventricular lead 108 is electrically coupled to a right ventricular tip electrode 128, a right ventricular ring electrode 130, a right ventricular (RV) coil electrode 132, and an SVC coil electrode 134. Typically, the right ventricular lead 108 is transvenously inserted into the heart 102 to place the right ventricular tip electrode 128 in the right ventricular apex so that the RV coil electrode 132 will be positioned in the right ventricle and the SVC coil electrode 134 will be positioned in the superior vena cava. Accordingly, the right ventricular lead 108 is capable of receiving cardiac signals, and delivering stimulation in the form of pacing and shock therapy to the right ventricle.

Figure 2:
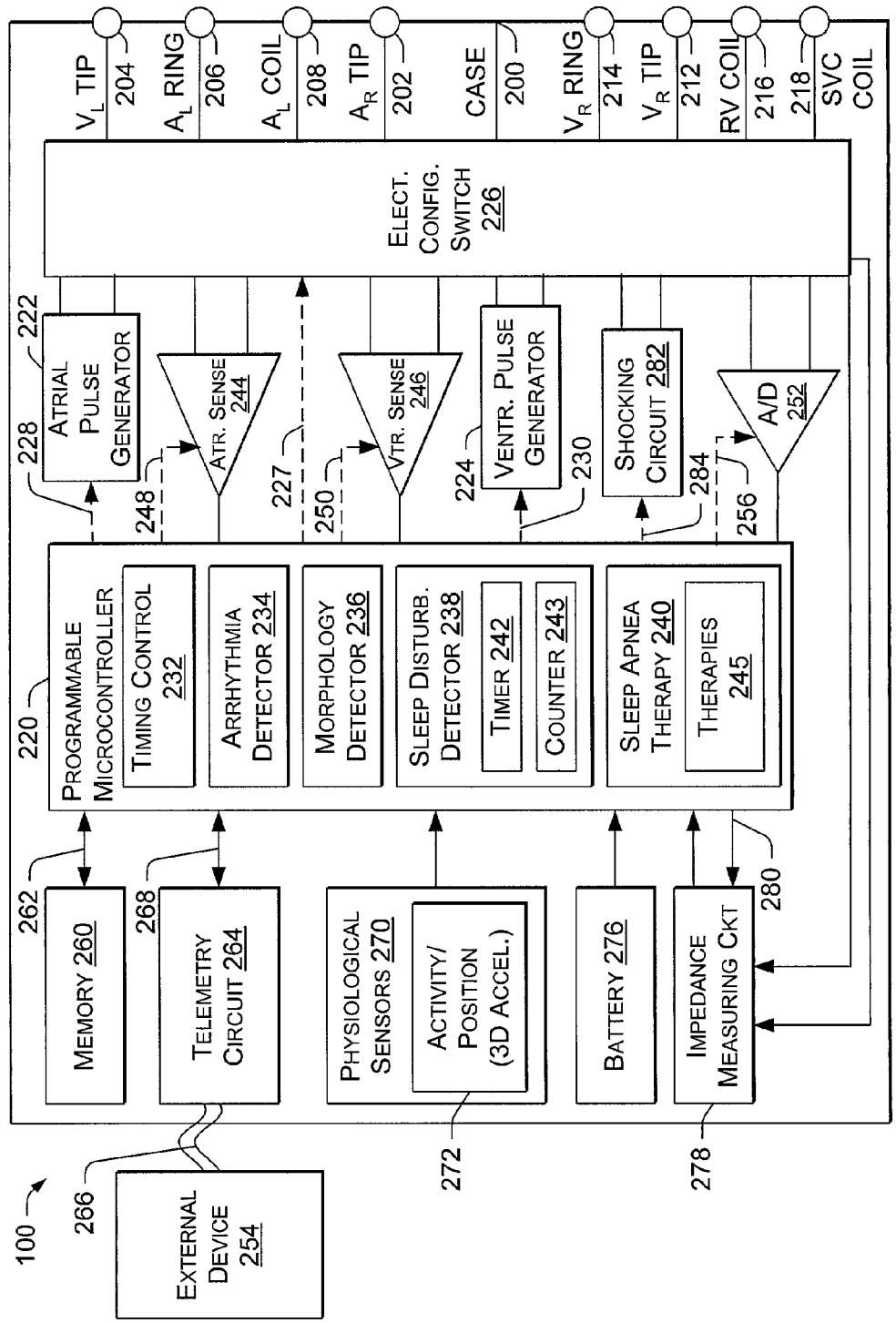
FIG. 2 is a functional block diagram of the multi-chamber implantable cardiac device.

FIG. 2 shows an exemplary, simplified block diagram depicting various components of the implantable cardiac device 100. The components are housed in housing 200, which is often referred to as the "can", "case", "encasing", or "case electrode", and may be programmably selected to act as the return electrode for unipolar modes. Housing 200 may further be used as a return electrode alone or in combination with one or more of the coil electrodes 126, 132 and 134 for shocking purposes. Housing 200 further includes a connector (not shown) having a plurality of terminals 202, 204, 206, 208, 212, 214, 216, and 218 (shown schematically and, for convenience, the names of the electrodes to which they are connected are shown next to the terminals), including:

- a right atrial tip terminal ($A_R$ TIP) 202 for atrial tip electrode 120;
- a left ventricular tip terminal ($V_L$ TIP) 204 for left ventricular tip electrode 122;
- a left atrial ring terminal ($A_L$ RING) 206 for left atrial ring electrode 124;
- a left atrial shocking terminal ($A_L$ COIL) 208 for left atrial coil electrode 126;
- a right ventricular tip terminal ($V_R$ TIP) 212 for right ventricular tip electrode 128;
- a right ventricular ring terminal ($V_R$ RING) 214 for right ventricular ring electrode 130;
- a right ventricular shocking terminal (RV COIL) 216 for RV coil electrode 132; and
- an SVC shocking terminal (SVC COIL) 218 for SVC coil electrode 134.

The implantable cardiac device 100 includes a programmable microcontroller 220 that controls various operations of the ICTD, including cardiac monitoring and stimulation therapy. Microcontroller 220 includes a microprocessor (or equivalent control circuitry), RAM and/or ROM memory, logic and timing circuitry, state machine circuitry, and I/O circuitry.

Device 100 further includes an atrial pulse generator 222 and a ventricular pulse generator 224 that generate pacing stimulation pulses for delivery by the right atrial lead 104, the coronary sinus lead 106, and/or the right ventricular lead 108 via an electrode configuration switch 226. The switch 226 includes multiple switches for connecting the desired electrodes to the appropriate I/O circuits, thereby providing complete electrode programmability. Accordingly, switch 226, in response to a control signal 227 from the microcontroller 220, determines the polarity of the stimulation pulses (e.g., unipolar, bipolar, combipolar, etc.) by selectively closing the appropriate combination of switches. To provide stimulation therapy in each of the four chambers of the heart, the atrial and ventricular pulse generators 222 and 224 may include dedicated, independent pulse generators, multiplexed pulse generators, or shared pulse generators. The pulse generators 222 and 224 are controlled by the microcontroller 220 via appropriate control signals 228 and 230, respectively, to trigger or inhibit the stimulation pulses.

Microcontroller 220 is illustrated as including timing control circuitry 232 to control the timing of the stimulation pulses (e.g., pacing rate, atrio-ventricular (AV) delay, atrial interconduction (A—A) delay, or ventricular interconduction (V—V) delay, etc.). The timing control circuitry may also be used for the timing of refractory periods, blanking intervals, noise detection windows, evoked response windows, alert intervals, marker channel timing, and so on.

Microcontroller 220 is also equipped with an arrhythmia detector 234, a morphology detector 236, a sleep disturbance detector 238, and a sleep apnea therapy module 240. The sleep disturbance detector 238 is configured to use sleep disturbance as a metric for detecting and potentially treating episodes of sleep apnea that occur while the patient is at rest. More particularly, the sleep disturbance detector 238 monitors patient activity while the patient is resting to detect short durations of heightened activity. Brief, heightened activity is a sleep disturbance that may be linked to an episode of sleep apnea. For instance, when the patient undergoes an episode of sleep apnea, the patient typically stops breathing for a duration of 30 to 60 seconds. When coming out of the episode, the patient often gasps for breath or jerks in some manner that causes a rapid change in the instantaneous activity signal. The sleep disturbance detector 238 detects these sudden changes in the instantaneous activity signal.

In one implementation, the sleep disturbance detector 238 detects when the instantaneous signal exceeds one or more predefined thresholds. The sleep disturbance detector 238 includes a timer 242 to time duration of the heightened activity above this threshold. If the duration is less than a predefined period (e.g., 30 sec.), the detector 238 identifies the heightened activity as sleep disturbance, which is suggestive of sleep apnea. If the duration is longer than the period (e.g., >30 sec.), the activity is deemed to be a wakeful or conscious movement, such as sitting up to get a drink of water or standing up following rest, and is not identified as sleep disturbance.

A counter 243 counts each event identified as sleep disturbance to track the number of sleep disturbance events that occur during a predetermined timeframe (e.g., resting period, 24 hours, etc.). The raw count is one type of sleep disturbance metric that can be used to ascertain the severity of sleep apnea. Another is to compute the frequency by determining the number of sleep disturbances occurring within the timeframe. A patient who experiences a higher number or a higher frequency of sleep disturbances (i.e., a higher number detected in a given period) can be said to have a more severe case of sleep apnea than a patient who experiences fewer or a lower frequency of sleep disturbances. The count is stored in the device memory, along with other diagnostics.

The sleep apnea therapy module 240 prescribes one or more pacing therapies 245 that can be administered in response to detection of sleep apnea. For example, the therapies might include overdrive pacing in which the pacing rate is increased by some fixed or adjustable amount. The responsive pacing may be applied for a period of time, or a predetermined number of beats, or until the sleep apnea episode has concluded. The therapies might call for different degrees of gradually decreasing the pacing rate to the intrinsic rate of the resting patient. As will be described below in more detail, the sleep apnea therapy module 240 administers different therapies 245 during an evaluation timeframe and evaluates how each therapy affects the sleep disturbance metrics. For example, therapies that lower the number or frequency of sleep disturbance (i.e., less events are detected in the period) are considered more effective than therapies that fail to lower the number or frequency.

The components 234–245 may be implemented in hardware as part of the microcontroller 220, or as software/firmware instructions programmed into the device and executed on the microcontroller 220 during certain modes of operation. Although not shown, the microcontroller 220 may further include other dedicated circuitry and/or firmware/software components that assist in monitoring various conditions of the patient's heart and managing pacing therapies.

Atrial sensing circuits 244 and ventricular sensing circuits 246 may also be selectively coupled to the right atrial lead 104, coronary sinus lead 106, and the right ventricular lead 108, through the switch 226 to detect the presence of cardiac activity in each of the four chambers of the heart. The sensing circuits 244 and 246 may include dedicated sense amplifiers, multiplexed amplifiers, or shared amplifiers. Switch 226 determines the "sensing polarity" of the cardiac signal by selectively closing the appropriate switches. In this way, the clinician may program the sensing polarity independent of the stimulation polarity. Each sensing circuit 244 and 246 may employ one or more low power, precision amplifiers with programmable gain and/or automatic gain control, bandpass filtering, and threshold detection circuitry to selectively sense the cardiac signal of interest. The automatic gain control enables the device 100 to sense low amplitude signal characteristics of atrial or ventricular fibrillation.

The outputs of the atrial and ventricular sensing circuits 244 and 246 are connected to the microcontroller 220 which, in turn, is able to trigger or inhibit the atrial and ventricular pulse generators 222 and 224 in a demand fashion in response to the absence or presence of cardiac activity in the appropriate chambers of the heart. The sensing circuits 244 and 246 receive control signals from the microcontroller 220 over signal lines 248 and 250 for purposes of controlling the gain, threshold, polarization charge removal circuitry (not shown), and the timing of any blocking circuitry (not shown) coupled to the inputs of the sensing circuits.

Cardiac signals are supplied to an analog-to-digital (A/D) data acquisition system 252, which is configured to acquire intracardiac electrogram signals, convert the raw analog data into a digital signal, and store the digital signals for later processing and/or telemetric transmission to an external device 254. The data acquisition system 252 is coupled to the right atrial lead 104, the coronary sinus lead 106, and the right ventricular lead 108 through the switch 226 to sample cardiac signals across any pair of desired electrodes.

The data acquisition system 252 is coupled to the microcontroller 220, or other detection circuitry, to assist in detecting an evoked response from the heart 102 in response to an applied stimulus, which is otherwise known as detecting "capture". Capture occurs when an electrical stimulus applied to the heart is of sufficient energy to depolarize the cardiac tissue, thereby causing the heart muscle to contract.

The microcontroller 220 detects a depolarization signal during a window following a stimulation pulse, the presence of which indicates that capture has occurred. The microcontroller 220 enables capture detection by triggering the ventricular pulse generator 224 to generate a stimulation pulse, starting a capture detection window using the timing control circuitry 232 within the microcontroller 220, and enabling the data acquisition system 252 via control signal 256 to sample the cardiac signal that falls in the capture detection window and, based on the amplitude, determines if capture has occurred.

Capture detection may occur on a beat-by-beat basis or on a sampled basis. A capture threshold search can desirably be performed once a day during at least the acute phase (e.g., the first 30 days) and less frequently thereafter. A capture threshold search would begin at a desired starting point (either a high energy level or the level at which capture is currently occurring) and decrease the energy level until capture is lost. The value at which capture is lost is known as the capture threshold. Thereafter, a safety margin is added to the capture threshold.

The microcontroller 220 is further coupled to a memory 260 by a suitable data/address bus 262. The programmable operating parameters used by the microcontroller 220 are stored in memory 260 and used to customize the operation of the device 100 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 102 within each respective tier of therapy.

The operating parameters of the implantable device 100 may be non-invasively programmed into the memory 260 through a telemetry circuit 264 in telemetric communication via communication link 266 with the external device 254, such as a programmer, transtelephonic transceiver, or a diagnostic system analyzer. The microcontroller 220 activates the telemetry circuit 264 with a control signal 268. The telemetry circuit 264 allows intracardiac electrograms and status information relating to the operation of the device 100 (as contained in the microcontroller 220 or memory 260) to be sent to the external device 254 through an established communication link 266.

The memory 260 is also used to store the sleep disturbance metrics, such as the number of events counted by counter 243 and any computed frequencies derived by determining the number of events that occur within a predetermined timeframe. The device uses the communication link 266 to upload this sleep disturbance metrics from the memory 260 to the external device 254, where the metrics can be analyzed by an attending physician or other caregiver.

The implantable cardiac device 100 can further include one or more physiologic sensors 270. Such sensors are commonly referred to as "rate-responsive" sensors because they are typically used to adjust pacing stimulation rates according to the exercise state of the patient. However, the physiological sensor(s) 270 may further be used to detect changes in cardiac output, changes in the physiological condition of the heart, diurnal changes in activity (e.g., detecting sleep and wake states), or respiration activity (e.g., minute ventilation). The microcontroller 220 responds to changes sensed by the sensor(s) 270 by adjusting various pacing parameters (such as rate, AV Delay, V—V Delay, etc.) at which the atrial and ventricular pulse generators 222 and 224 generate stimulation pulses. While shown as being included within the device 100, the physiologic sensor(s) 270 may also be external to the device 100, yet still be implanted within or carried by the patient. Examples of physiologic sensors that may be implemented in device 100 include sensors that, for example, sense respiration rate, pH of blood, ventricular gradient, minute ventilation, and so forth.

In the illustrated implementation, the physiological sensors 270 include sensors for detecting patient activity and/or patient position. Any sensor capable of sensing such changes, either directly or indirectly, may be used. In particular, the physiological sensors 270 include an activity/position sensor 272 to detect movement in the patient's position. The activity/position sensor 272 may be implemented in many ways, including as an activity sensor, a 3D accelerometer, a posture sensor, and a position sensor. In one configuration, the accelerometer output signal is bandpass-filtered, rectified, and integrated at regular timed intervals. The processed accelerometer signal is used as a raw activity signal. The device derives an activity measurement based on the raw activity signal at intervals timed according to the cardiac cycle, then determines an activity variance parameter. One or both of the activity signal and the activity variance signal is used to detect patient state, for example, from among sleeping, waking, resting, and exercise state. A large activity variance signal is indicative of a prolonged exercise state. Low activity and activity variance signals are indicative of a prolonged resting state.

Another sensor that may be used is one that detects activity variance, wherein an activity sensor is monitored diurnally to detect the low variance in the measurement corresponding to the sleep state. For a complete description of the activity variance sensor, the reader is directed to U.S. Pat. No. 5,476,483 (Bornzin et. al., issued Dec. 19, 1995, which is hereby incorporated by reference.

Signals generated by the activity/position sensor 272 are passed to the microcontroller 220 for analysis by the sleep disturbance detector 238. Such signals can be used to determine whether the patient is at rest, whether the patient is experiencing sleep disturbance or is transitioning out of the rest state, and whether to invoke any responsive therapy prescribed by the sleep apnea therapy module 240.

The implantable cardiac device 100 additionally includes a battery 276 that provides operating power to all of the components shown in FIG. 2. The battery 276 is capable of operating at low current drains for long periods of time (e.g., less than 10 µA), and is capable of providing high-current pulses (for capacitor charging) when the patient requires a shock pulse (e.g., in excess of 2 A, at voltages above 2 V, for periods of 10 seconds or more). The battery 276 also desirably has a predictable discharge characteristic so that elective replacement time can be detected. As one example, the device 100 employs lithium/silver vanadium oxide batteries.

The device 100 can further include magnet detection circuitry (not shown), coupled to the microcontroller 220, to detect when a magnet is placed over the stimulation device 100. A magnet may be used by a clinician to perform various test functions of the stimulation device 100 and/or to signal the microcontroller 220 that the external programmer 254 is in place to receive or transmit data to the microcontroller 220 through the telemetry circuits 264.

The device 100 further includes an impedance measuring circuit 278 that is enabled by the microcontroller 220 via a control signal 280. The impedance measuring circuit 278 is used for many things, including: lead impedance surveillance during the acute and chronic phases for proper lead positioning or dislodgement; detecting operable electrodes and automatically switching to an operable pair if dislodgement occurs; measuring thoracic impedance for determining shock thresholds; detecting when the device has been implanted; measuring stroke volume; and detecting the opening of heart valves; measuring respiration-related parameters, such as respiration rate, minute ventilation, respiration signal amplitude, and tidal volume; and so forth.

The device 100 can be operated as an implantable cardioverter/defibrillator (ICD) device, which detects the occurrence of an arrhythmia and automatically applies an appropriate electrical shock therapy to the heart aimed at terminating the detected arrhythmia. To this end, the microcontroller 220 further controls a shocking circuit 282 by way of a control signal 284. The shocking circuit 282 generates shocking pulses of low (e.g., up to 0.5 Joules), moderate (e.g., 0.5–10 Joules), or high energy (e.g., 11 to 40 Joules), as controlled by the microcontroller 220. Such shocking pulses are applied to the patient's heart 102 through at least two shocking electrodes selected, for example, from the left atrial coil electrode 126, the RV coil electrode 132, and/or the SVC coil electrode 134. As noted above, the housing 200 may act as an active electrode in combination with the RV electrode 132, or as part of a split electrical vector using the SVC coil electrode 134 or the left atrial coil electrode 126 (i.e., using the RV electrode as a common electrode).

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5–40 Joules), delivered asynchronously (since R-waves may be too disorganized), and pertaining exclusively to the treatment of fibrillation. Accordingly, the microcontroller 220 is capable of controlling the synchronous or asynchronous delivery of the shocking pulses.

Sleep Disturbance Detection

Figure 3:
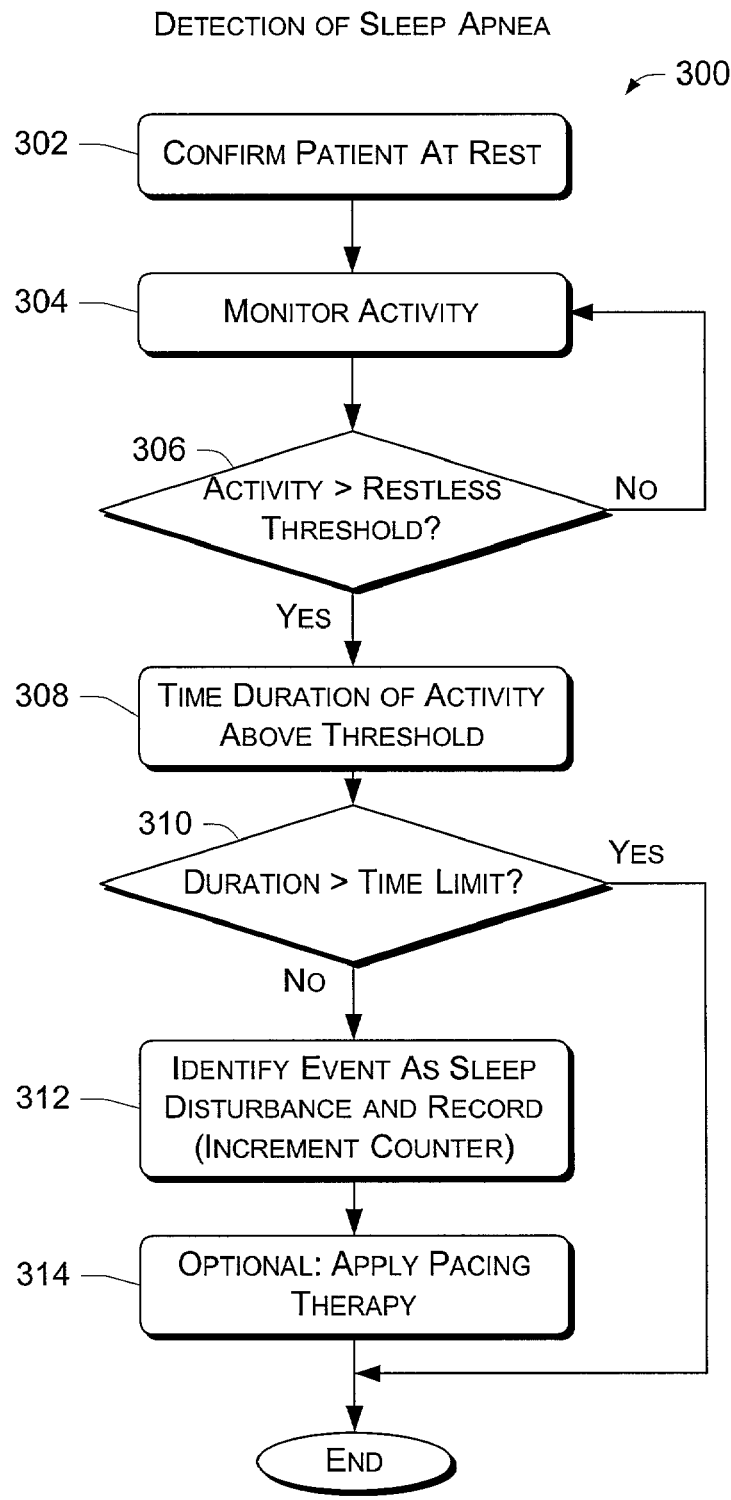
FIG. 3 is a flow diagram of a process for detecting sleep disturbances.

FIG. 3 shows a process 300 for detecting sleep disturbance. According to this process, the implantable cardiac device is programmed to monitor short term activity changes that occur while a patient is at rest to produce a sleep disturbance metric that is useful in analyzing and/or treating sleep apnea. This process 300 may be implemented in connection with any suitably configured device, although it will be described as being executed by the implantable cardiac device 100 of FIGS. 1 and 2. In the flow diagram, the operations are summarized in individual blocks. The operations may be performed in hardware and/or as machine-readable instructions (software or firmware) that can be executed by a processor.

At block 302, the implantable cardiac therapy device 100 confirms when a patient is at rest. There are many ways to implement this function. One approach is to monitor an activity sensor and confirm that a patient is at rest when the patient has been inactive for a predetermined amount of time. Another approach is to monitor signals from a position/posture sensor to identify when the patient stops moving for a prolonged period of time, or when the patient reclines to a supine position. For purposes of continuing discussion, the device monitors a raw activity signal from the accelerometer and/or derives an activity variance parameter from the activity signal. One or both of the activity signal and the activity variance signal is then used to detect different patient states, such as resting and non-resting states.

At block 304, the device monitors for activity that might occur while the patient is resting. In one implementation, the device monitors the instantaneous activity signal for any sudden, but brief, changes in the signal that rise to a level suggestive of sleep disturbance. Accordingly, at block 306, the device determines whether the activity signal exceeds a threshold indicative of restlessness. This threshold is preset above the low level of activity sensed during normal resting periods.

Figure 4:
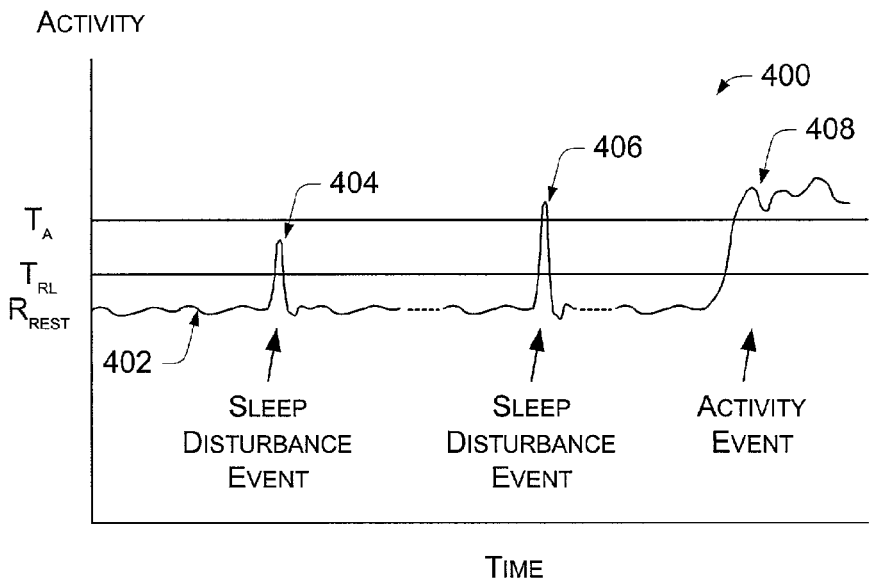
FIG. 4 illustrates an example of an activity signal pattern that may be used to detect sleep disturbances.

To better illustrate detection block 306, FIG. 4 shows an exemplary activity signal pattern 400 of a patient. When the patient is resting, the activity signal A is low for a prolonged period of time, with very little activity, as indicated by pattern 402. Above this intrinsic rest rate are two thresholds: a restless threshold $T_{RL}$ and an activity threshold $T_A$. The values for the thresholds vary depending upon the desired implementation, as well as conditions of each patient. In the illustrated implementation, the restless threshold $T_{RL}$ is at a slightly lower level of activity than the activity threshold. In other implementations, the difference between may be greater or smaller, or the restless threshold $T_{RL}$ may be set to equal to the activity threshold $T_A$.

As indicated by the "no" branch from block 306, the device continues to monitor patient activity until the activity signal exceeds the restless threshold $T_{RL}$. When the activity signal exceeds the restless threshold $T_{RL}$, the sleep disturbance detector 238 initiates the timer 242 to begin timing the duration that the signal is above the restless threshold (block 308). At block 310, the sleep disturbance detector 238 determines whether the duration being timed by timer 242 exceeds a preset time limit. This time-based decision differentiates short-term sleep disturbances from more meaningful and potentially wakeful activity. The time limit is preset to a short period, such as 20–40 seconds, with 30 seconds being a suitable default. The theory underlying this time determination is that brief periods of activity are most likely attributable to sleep disturbance (e.g., rolling over, twitches, gasps for breath, etc.), whereas longer lasting activity might be indicative of more than just disturbance, such as sitting up in bed or waking up. Accordingly, if the activity exceeds the time limit (i.e., the "yes" branch from block 310), the sleep disturbance detector 238 determines that the activity represents something other than sleep disturbance and the process ends. On the other hand, if the activity does not exceed the preset time limit (i.e., the "no" branch from block 310), the sleep disturbance detector 238 identifies the activity as sleep disturbance and increments the counter 243 (block 312). The sleep disturbance events are then recorded in memory 260 and can be subsequently transmitted to the external device 254 for analysis by a physician.

Figures 5, 6, 7:
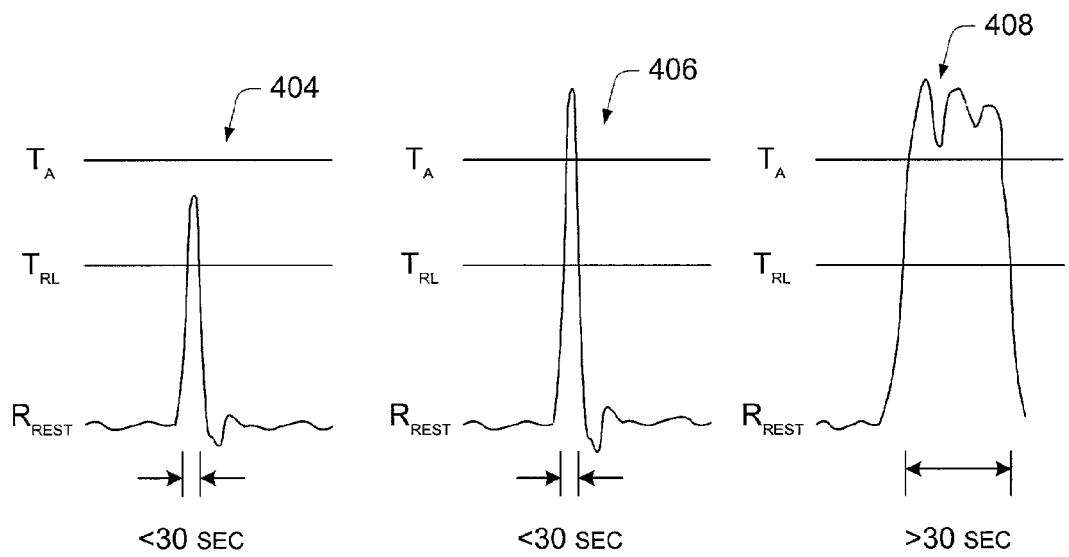
FIGS. 5–7 show different activity patterns of an instantaneous activity pattern that are indicative of sleep disturbance (FIGS. 5 and 6) and other forms of activity (FIG. 7).

FIGS. 4–7 illustrate different activity events that may be alternatively identified as sleep disturbance or other forms of activity. FIGS. 4 and 5 illustrate a first event 404 in which the activity signal exceeds the restless threshold $T_{RL}$ for less than the preset time limit (e.g., 30 seconds). This first event 404 is characterized as sleep disturbance. FIGS. 4 and 6 illustrate a second event 406 in which the activity signal exceeds both the restless threshold $T_{RL}$ and the higher activity threshold $T_A$, but for a short period of less than 30 seconds. Second event 406 is representative of a move severe or violent sleep disturbance due to the higher rate of activity. However, since the activity is so short and the pattern returns to normal sleep patterns, the event is characterized as sleep disturbance, albeit more violent than event 404. FIGS. 4 and 7 illustrate a third event 408 in which the activity signal exceeds both the restless threshold $T_{RL}$ and the higher activity threshold $T_A$ for a prolonged time period of more than 30 seconds. Third event 408 is representative of wakeful activity, such as sitting or standing up. This event fails the time determination of block 310 and thus, is not characterized as sleep disturbance.

As indicated by block 314, the device 100 can be configured to optionally administer pacing therapy to treat sleep apnea episodes that may be causing the sleep disturbance. For instance, one possible pacing response is to apply overdrive pacing, where the pacing rate is increased by a fixed amount above an intrinsic rate usually applied when the patient is at rest. As an alternative to increasing the pacing rate by a fixed amount, the device may be programmed to adjust the overdrive pacing rate using some target parameter. The overdrive pacing may be applied for a predetermined time period, or number of beats. It may then be gradually reduced.

The sleep disturbance metrics, such as frequency of occurrence, could prove useful to physicians who are trying to better understand sleep apnea in individual patients. Additionally, the metrics may be used to evaluate different forms of therapies to determine which therapies are effective at minimizing sleep disturbance (e.g., reducing the frequency of disturbance events), and hence indirectly improving quality of life for a patient who experiences sleep apnea. Evaluation of pacing therapies, in particular, is described in the following section.

Therapy Evaluation

As shown in block 314 of FIG. 3, the cardiac device can be programmed to administer a pacing therapy to treat sleep apnea. In addition, the device may be programmed, under supervision of a physician, to apply different types of pacing therapies on a patient to determine which therapies are effective at minimizing sleep disturbance.

Figure 8:
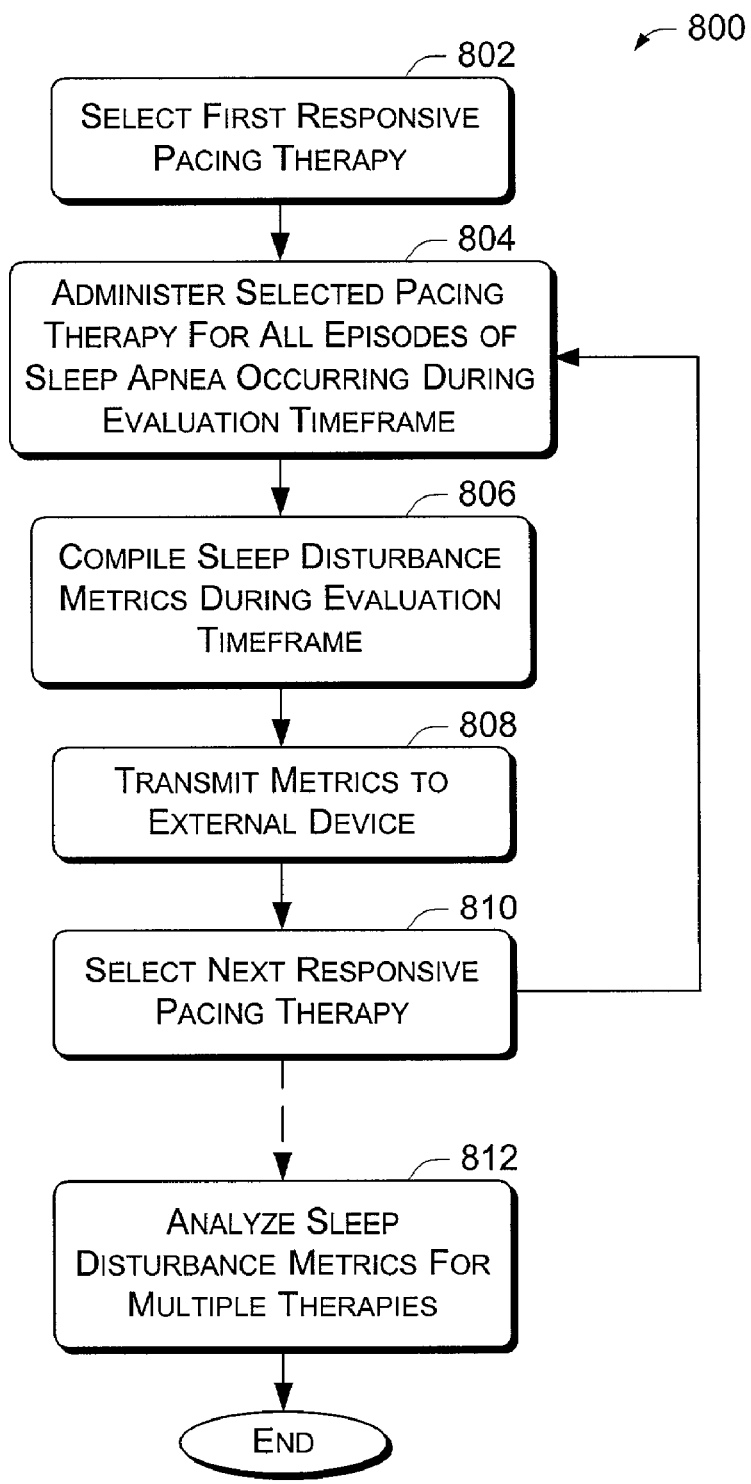
FIG. 8 is a flow diagram of a process for evaluating different pacing therapies for their impact on sleep disturbances.

FIG. 8 shows a process 800 for evaluating different pacing therapies in regards to their impact on sleep disturbance. As above, the evaluation process 800 will be described as being executed by the implantable cardiac device 100 of FIGS. 1 and 2. The operations may be performed in hardware and/or as machine-readable instructions (software or firmware) that can be executed by a processor.

At block 802, a first pacing therapy is selected under the direction of the physician. The pacing therapy may be pre-stored on the device, or programmed into the device for purposes of evaluation. At block 804, the sleep apnea therapy module 240 administers the selected pacing therapy for all episodes of sleep apnea that occur during a predefined evaluation timeframe. Sleep apnea may be detected in many ways, including using respiration-related signals (e.g., minute ventilation, tidal volume, respiration rate, etc.) and/or oxygen signals (e.g., $O_2$ sensor signal). The evaluation timeframe may be of any duration prescribed by the physician, with example timeframes being a 24 hour period or a week.

At block 806, the device 100 compiles sleep disturbance metrics (e.g., total number of sleep disturbance events, frequency of sleep disturbance events during rest periods, etc.) for all events that occur during the evaluation timeframe. The metrics are transmitted to the physician for review (block 808).

At block 810, a new pacing therapy is selected under the direction of the physician. For instance, the device may utilize another pre-stored therapy 245 or the physician may download another therapy into the device for the next trial. Process flow then returns to block 804, where the device administers the next selected pacing therapy for all episodes occurring in the evaluation timeframe.

At block 812, the sleep disturbance metrics collected for multiple different therapies are analyzed to determine which of the therapies is most effective at reducing the frequency and/or number of sleep disturbance events. Since these metrics act as a surrogate for sleep apnea, therapies that reduce the number or frequency of sleep disturbance events are expected to additionally treat sleep apnea. The analysis is performed, for example, on an external computing system, such as a programmer or other computer used by the physician. However, as memory and processing capabilities continue to improve, the analysis may be conducted at the implantable cardiac device for multiple different pacing therapies.

Conclusion

The foregoing discussion describes use of sleep disturbance metrics, derived by the implantable cardiac device, as a surrogate measure to discern severity of sleep apnea and to help evaluate whether various pacing therapies are effective for treating sleep apnea. With such techniques, effective therapies for treating apnea can be developed on a patient-by-patient basis.

Although the invention has been described in language specific to structural features and/or methodological acts, it is to be understood that the subject matter defined in the appended claims is not necessarily limited to the specific features or acts described. Rather, the specific features and acts are disclosed as exemplary forms of implementing the claimed invention.

The invention claimed is:

1. A method implemented by an implantable cardiac device, comprising:
    detecting a heightened level of patient activity while the patient is at rest;
    timing a duration of the heightened level of patient activity;
    in an event that the duration is less than a predefined time limit, identifying the heightened level of patient activity as sleep disturbance;
    administering multiple different pacing therapies to treat sleep apnea; and
    evaluating the pacing therapies based on how the pacing therapies affect the sleep disturbances.

2. A method as recited in claim 1, wherein the detecting comprises determining when a patient is in a reclined position and monitoring the patient's activity while the patient is in the reclined position.

3. A method as recited in claim 1, wherein the detecting comprises monitoring an instantaneous signal from an activity sensor.

4. A method as recited in claim 1, wherein the time limit is approximately forty seconds.

5. A method as recited in claim 1, further comprising counting the sleep disturbances.

6. A method as recited in claim 1, further comprising storing at least one of a count or a frequency of the sleep disturbances.

7. A computer readable medium having computer-executable instructions that, when executed, direct an implantable cardiac device to perform the method as recited in claim 1.

8. A method comprising:
    determining that a patient is at rest;
    while the patient is at rest,
    monitoring an instantaneous activity signal indicative of a patient's activity;
    detecting when the instantaneous activity signal exceeds a threshold;
    timing a duration that the instantaneous activity signal exceeds the threshold;
    in an event that the instantaneous activity signal exceeds the threshold for less than a preset time, recording the patient's activity as a sleep disturbance;
    administering multiple different pacing therapies to treat sleep apnea;
    collecting sleep disturbance metrics for individual pacing therapies; and
    evaluating the pacing therapies based on how the pacing therapies affect the sleep disturbance metrics.

9. A method as recited in claim 8, further comprising determining a frequency of sleep disturbances that occur within a predetermined timeframe.

10. A method as recited in claim 8, further comprising counting the sleep disturbances.

11. A method as recited in claim 8, further comprising identifying the patient's activity as meaningful activity if the instantaneous activity signal exceeds the threshold for more than the preset time.

12. A computer readable medium having computer-executable instructions that, when executed, direct an implantable cardiac device to perform the method as recited in claim 8.

13. An implantable cardiac device comprising:
    sensing circuitry to sense a patient's activity;
    a sleep disturbance detector to detect when a patient, who is at rest, is experiencing sleep disturbance based on the patient's activity;
    a therapy module to prescribe a pacing therapy for treating sleep apnea from among multiple different pacing therapies;
    a pulse generator to generate pacing pulses according to the prescribed pacing therapy for an evaluation timeframe; and
    the sleep disturbance detector counting a number of sleep disturbances experienced during the evaluation timeframe of the prescribed pacing therapy.

14. An implantable cardiac device as recited in claim 13, wherein the sensing circuitry comprises at least one of an activity sensor, a position sensor, an accelerometer, and a posture sensor.

15. An implantable cardiac device as recited in claim 13, wherein the sleep disturbance detector is configured to detect the sleep disturbance by determining when the patient's activity rises above a threshold for less than approximately 40 seconds.

16. An implantable cardiac device as recited in claim 13, further comprising a memory to store events of sleep disturbance.

17. An implantable cardiac device comprising:
    an activity sensor to sense a patient's activity;
    a processor to confirm that the patient is at rest based on the patient's activity and while the patient is resting, to detect one or more sleep disturbances that occur when the patient's activity rises above a threshold for less than a preset time limit;
    a memory to store disturbance data pertaining to the sleep disturbances detected by the processor;
    a therapy module to prescribe a pacing therapy for treating sleep apnea from among multiple different pacing therapies;
    a pulse generator to generate pacing pulses according to the prescribed pacing therapy for an evaluation timeframe; and
    the sleep apnea detector measuring durations of episodes experienced during the evaluation timeframe of the prescribed pacing therapy.

18. An implantable cardiac device as recited in claim 17, further comprising a second sensor to detect when the patient is in a reclined position, the second sensor being selected from a group comprising a position sensor, a posture sensor, and an accelerometer.

19. An implantable cardiac device as recited in claim 17, wherein the processor is configured to count a number of sleep disturbances that occur during a predetermined time period.

20. An implantable cardiac device as recited in claim 19, wherein the processor derives a frequency of sleep disturbances based on the number of sleep disturbances that occur during the predetermined time period.

21. An implantable cardiac device as recited in claim 17, wherein the processor comprises a timer to time duration of the patient's activity to determine whether the duration is less than the preset time limit.

22. An implantable cardiac device comprising:
- activity detection means for detecting when a patient's activity rises above a preset threshold;
- timing means for timing a duration that the patient's activity is above the preset threshold;
- identification means for identifying the patient's activity as sleep disturbance in an event that the patient's activity is above the preset threshold for less than a time limit; and
- apnea therapy means for administering a pacing therapy to counteract the sleep apnea from among a multiple of different pacing therapies.

23. An implantable cardiac device as recited in claim 22, wherein the activity detection means comprises:
- a sensor to output an activity signal; and
- a processor to determine when the activity signal exceeds the preset threshold.

24. An implantable cardiac device as recited in claim 23, wherein the sensor is selected from one or more sensors selected from a group of sensors comprising an activity sensor, an accelerometer, a position sensor, and a posture sensor.

25. An implantable cardiac device as recited in claim 22, wherein the activity detection means comprises:

- a posture sensor to detect when the patient is in a reclined position;
- an activity sensor to detect the patient's activity while the patient is in the reclined position; and
- a processor to determine when the activity signal, taken while the patient is in the reclined position, exceeds the preset threshold.

26. An implantable cardiac device as recited in claim 22, further comprising counting means for counting a number of sleep disturbances that occur during a predefined timeframe.

27. An implantable cardiac device as recited in claim 22, further comprising storage means for storing data pertaining to events identified as sleep disturbance.

28. An implantable cardiac device as recited in claim 27, further comprising transmission means for transmitting the data to an external device.

29. An implantable and programmable cardiac device having a memory and a processor, the cardiac device being programmed to perform tasks comprising:
- detecting a heightened level of patient activity while the patient is at rest;
- timing a duration of the heightened level of patient activity;
- in an event that the duration is less than a predefined time limit, identifying the heightened level of patient activity as sleep disturbance; and
- administering different pacing therapies for treating sleep apnea and collecting sleep disturbance metrics during individual therapies to evaluate effectiveness of the different pacing therapies.

30. An implantable and programmable cardiac device as recited in claim 29, further programmed to perform tasks comprising detecting the heightened level of patient activity by comparing an instantaneous activity signal to a threshold.

31. An implantable and programmable cardiac device as recited in claim 29, further programmed to perform tasks comprising counting a number of sleep disturbances that occur within a predetermined timeframe.

* * * * *